United States Patent [19]

John

[11] 4,279,258
[45] Jul. 21, 1981

[54] RAPID AUTOMATIC ELECTROENCEPHALOGRAPHIC EVALUATION

[76] Inventor: E. Roy John, 930 Greacen La., Mamaroneck, N.Y. 10546

[21] Appl. No.: 134,309

[22] Filed: Mar. 26, 1980

[51] Int. Cl.³ .............................................. A61B 5/04
[52] U.S. Cl. ................................................. 128/731
[58] Field of Search ............................... 128/731, 732

[56] References Cited

U.S. PATENT DOCUMENTS

| | | | |
|---|---|---|---|
| 3,498,287 | 3/1970 | Ertl | 128/731 |
| 3,725,690 | 4/1973 | Hjorth | 128/731 |
| 3,809,069 | 5/1974 | Bennett | 128/731 |
| 3,863,625 | 2/1975 | Viglione et al. | 128/732 |
| 4,214,591 | 7/1980 | Sato et al. | 128/731 |

Primary Examiner—William E. Kamm
Attorney, Agent, or Firm—Eliot S. Gerber

[57] ABSTRACT

The rapid automatic examination and evaluation of large numbers of subjects by electroencephalography is accomplished by removably securing electrodes to the head of each subject under test to provide a plurality of channels of brain wave information corresponding to different head regions. The brain wave signals are amplified, converted into digital form, and the relative power in each of a plurality of frequency bands for each head region is automatically compared with a set of comparative relative power data derived from a normal population by computing a Z-transform. The results of that comparison are then displayed.

11 Claims, 2 Drawing Figures

RAPID AUTOMATIC ELECTROENCEPHALOGRAPHIC EVALUATION

BACKGROUND OF THE INVENTION

The present invention relates to electroencephalography (EEG) and more particularly to methods for the rapid screening of large numbers of subjects.

At the present time there does not exist a program in the United States to determine, using rapid and widespread automatic evaluation methods, if learning or behavioral problems of school age children are due to organic brain dysfunction. A number of tests, administered within school systems, attempt to distinguish learning disabled children from other children. Some of these tests, for example, the Wechsler and Stanford-Binet scales have been criticized as being culturally biased, i.e., relying upon culturally determined skills such as the use of language rather than reflecting the innate capability of the child. Other of the tests have been criticized as relying upon the subjective judgments of the teacher or psychologist administering the test. In all cases, however, since the tests rely upon the cooperation of the child and the child's attitude and attention span, such tests may give results which do not reflect the child's mental ability. Those tests which are utilized to distinguish learning disabled children from other children do not differentially identify children having unusual brain activity, since these tests evaluate products rather than underlying processes.

It has been suggested, as a goal for the future, that it would be advantageous if there were some practical and accurate system by which large numbers of children "at risk" for learning or behavioral problems may be tested to distinguish between those with organic brain dysfunction and those with social, motivational or emotional problems. There have not been any serious attempts to provide such a program, however, since presently the only accepted testing method involves a complex and prolonged battery of tests given by a trained neurologist. Such tests may include an electroencephalogram (EEG) which would be visually interpreted by the neurologist based upon his years of training. The shortage of trained neurologists, the fact that extremely high percentages of school children are at risk, and the expense of a program based upon extensive individual examination of children by such neurologists has precluded large-scale diagnostic evaluation using EEG examinations. Further, subjective evaluation of children's EEG's has been shown to generate a high percentage of false positive findings and to be poorly replicable.

A series of prior patents and patent applications naming the inventor of the present application as their inventor provides a considerable amount of background information and details of certain portions of the system used in the present invention; and consequently these patents and applications are specifically referred to below and incorporated herein by reference. The patents and applications are as follows:

| PATENTS | | |
|---|---|---|
| | Title | Issue Date |
| U.S. Pat. No. 3,696,308 | Method and System For Brain Wave Analysis | Oct. 10, 1972 |
| U.S. Pat. No. 3,705,297 | Signal Averager | Dec. 5, 1972 |
| U.S. Pat. No. 3,780,274 | Sensation-Cognition Computer Employing "T" Test Calculations | Dec. 25, 1973 |
| U.S. Pat. No. 3,901,215 | Method of Testing the Senses and Cognition of Subjects | Aug. 26, 1975 |
| U.S. Pat. No. 4,171,696 | Prevention of Distortion of Brainwave Data Due To Eye Movement or Other Artifacts | Oct. 23, 1979 |

| APPLICATIONS | | |
|---|---|---|
| | | Filing Date |
| Serial No. 873,118 | System and Method For Electrode Pair Derivations in Electroencephalography | Jan. 30, 1978 |
| Serial No. 918,730 now Pat. No. 4,188,956 | Method for the Analysis, Display and Classification of Multivariate Indices of Brain Function -- A Functional Electrophysiological Brain Scan | June 26, 1978 |
| Serial No. 918,731 now Pat. No. 4,216,781 | Methods of Electrophysiological Testing | June 26, 1978 |
| Serial No. 974,445, now Pat. No. 4,201,224 | Electroencephalographic Method and System For Quantitative Description of Patient Brain States | Dec. 29, 1978 |

U.S. Pat. No. 4,037,586 to James Grichnik entitled "Electroencephalograph Display" shows a visual display panel actuated in response to digital signals. The panel indicates to the operator which of the electrodes are providing the signals being processed, i.e., "the actual montage of electrodes or the patterns in which the electrodes are being scanned."

OBJECTIVES OF THE INVENTION

It is an objective of the present invention to provide a means utilizing an electroencephalographic system for accurately and quantitatively screening subjects to determine if they have indications of organic brain dysfunction.

It is a further objective of the present invention to provide such a means in which the tests may be administered by trained personnel who need not be medical doctors.

It is a further objective of the present invention to provide such a means in which the tests are not culturally biased, that is, they are equally valid regardless of the cultural background or language ability of the subject.

BRIEF DESCRIPTION OF THE DRAWINGS

Other objectives and features of the present invention will be apparent from the following detailed description which provides the inventor's presently known best mode of practicing the invention. The following detailed description should be taken in conjunction with the accompanying drawings.

In the drawings.

SUMMARY OF THE INVENTION

It is a feature of the present invention to provide a method in electroencephalography (EEG) for testing subjects to determine organic brain dysfunction by diffuse and local head region shifts in the EEG spectrum. The method comprises removably securing a plurality of electrodes to the head of the subject under test and amplifying the on-going signals representing brain waves from each of the electrodes during a resting period, when the subject has a minimum of external stimuli. The brain wave signals are converted into digital form and divided into a plurality of frequency bands. The power in each of the frequency bands is computed and converted to percentage total power, to provide frequency band relative power which is automatically compared with a set of comparative relative power data from a normal population using stored normative data or using the formula:

$$\bar{X} = a_0 + a_1 t^1 + a_2 t^2 + a_3 t^3 + a_4 t^4$$

where t is age related and the coefficients $a_0$–$a_4$ are determined by fitting a regression equation to the data from the normal population. The relative power data in each band are then Z-transformed relative to these norms to yield the probability that the observed values might be obtained from a normal person. The results are then displayed and consist of the value of the Z-transformation of the relative power in the delta, theta, alpha and beta frequency bands. Such a Z-transformation is defined by $$\frac{X - \bar{X}}{\sigma},$$

where X = relative (%) power in a particular frequency band, measured from the subject; $\bar{X}$ = average relative (%) power in the same frequency band, measured in a group of normal persons the same age as the subject, or computed from an age-regression equation for normal data; and $\sigma$ = standard deviation of the normal sample. An additional log transform log [X/100−X] may be used to obtain gaussian data distributions.

In one embodiment of the present invention the electrodes are pairs of electrodes connected to regions of the subject's head and the display is in sectors corresponding to the head regions. The display means preferably includes portions of illuminable panels corresponding in location to the local selected head regions. Each panel portion is illuminated with a light whose color depends upon the results of the computation.

DETAILED DESCRIPTION OF THE INVENTION

Figure 1:
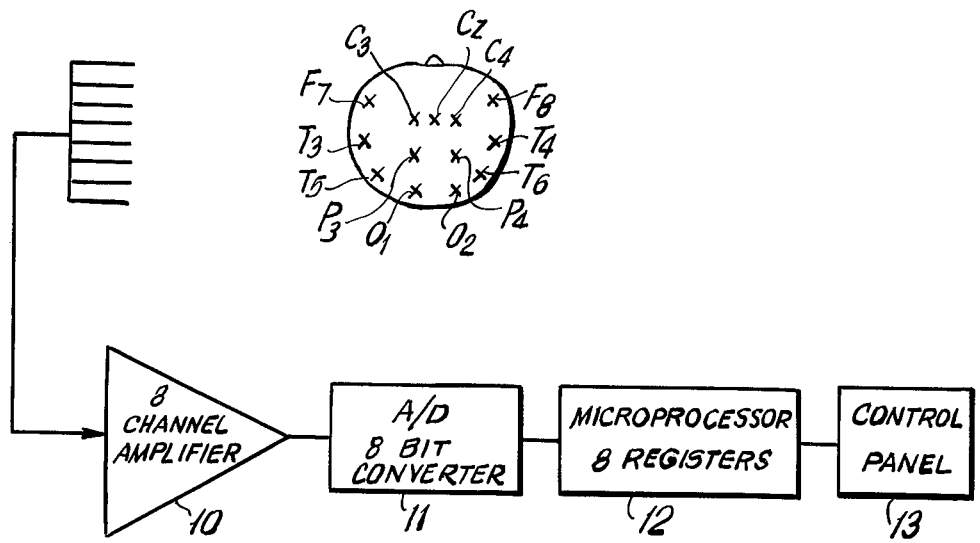
FIG. 1 is a block electronic schematic drawing of the system utilized in the present invention.

A system which is suitable for rapid automatic screening is shown in block diagram in FIG. 1. The description given below of the various devices constituting the system is intended as a guide for a suitable screening computer system based upon the experiments that have been conducted. However, it will be understood that, as improvements are made in the various system components and devices, they may be incorporated in the system within the scope of the present invention. Various elements of the system, for example, muscle artifact suppression, and further details concerning other elements of the system, may be found in the patents and pending patent applications referred to above.

The detection of the patient's brainwaves may be made using conventional electrode placement and conventional fixed-gain low-noise isolated amplifiers. However, the electrode placement and amplifier system described below may be utilized.

The input to the system utilizes the conventional system of electrode placement on the head of the patient. Electrodes may be affixed singly or on bands. For example, one band may encircle the head and carry electrodes corresponding to the International 10/20 System positions $F_7$, $T_3$, $T_5$, $O_1$, $O_2$, $T_6$, $T_4$, $F_8$, and also a frontal ground. A second band goes from the positions of $T_3$ to $T_4$ and carries electrodes at positions $C_3$ and $C_4$. A third band goes from the position of $T_5$ to $T_6$ and carries electrodes at positions $P_3$ and $P_4$. A pair of electrodes is placed trans-orbitally to monitor eye movements and blinks.

The electrodes are connected to a fixed gain EEG amplifier 10 having eight input channels. The chart below shows the preferred arrangement of the head electrodes and their relationship to the input channels of the EEG amplifier. Although the EEG amplifier is shown in FIG. 1 as a single amplifier, it consists of an independent amplifier for each of the channels. Each of the amplifiers has a gain of 10,000, 106 dB common mode rejection ratio, 4 megohm input impedance, and a frequency response over the range 0.5–50 Hz. The preferred arrangement of the head electrodes to the eight channels of the amplifier 10 is as follows:

| (1 and 2) $F_7T_3/F_8T_4$ | (3 and 4) $T_3T_5/T_4T_6$ |
|---|---|
| (5 and 6) $C_3C_2/C_4C_z$ | (7 and 8) $P_3O_1/P_4O_2$ |

The amplifier 10 is connected to an analog-to-digital (A/D) converter 11 which is an 8-bit converter having a sample rate of 100 per second. The data is multiplexed by the A/D converter 11 and communicated to the microprocessor 12 where it is demultiplexed and stored in the registers of the microprocessor. Preferably the microprocessor core memory is organized so that provision is made for 8 "buffer" registers each having a 500-bit capacity.

Prior to placement of electrodes on the subject, the system should be calibrated. Such calibration may be accomplished using sine waves of 2.5, 5.5, 10 and 15.7 Hz produced by four sine wave generators, each of the sine waves reaching 20 μv peak to peak. The four sine waves are mixed into a composite signal which contains 25% of its power in each of the $\Delta 2$, $\theta$, $\alpha$, and $\beta_1$ bands (as defined subsequently). The operator pushes "calibrate" button 7 to provide a five-second calibration signal feeding into each amplifier. Both the absolute and the relative powers are checked against a standard and should be within 5% plus or minus of that standard to be considered satisfactory. If the calibration is satisfactory, "calibration OK" light 8 goes on. If unsatisfactory, "calibration unacceptable" light 9 goes on.

The impedance of each head electrode should be tested to insure that the electrodes have been properly placed on the subject. The control panel 13 has an "impedance test" button 14 which is actuated so that if the impedance is too low or too high it will be indicated on the panel 13 by light 15. If the impedance of some lead is too high, i.e., above a specified level, for example, 10,000 ohms, a red light goes on at the position of a head diagram 30 corresponding to that lead. Preferably the lights of the panel 13 and of the head diagram 30 are light emitting diodes (LED).

Figure 2:
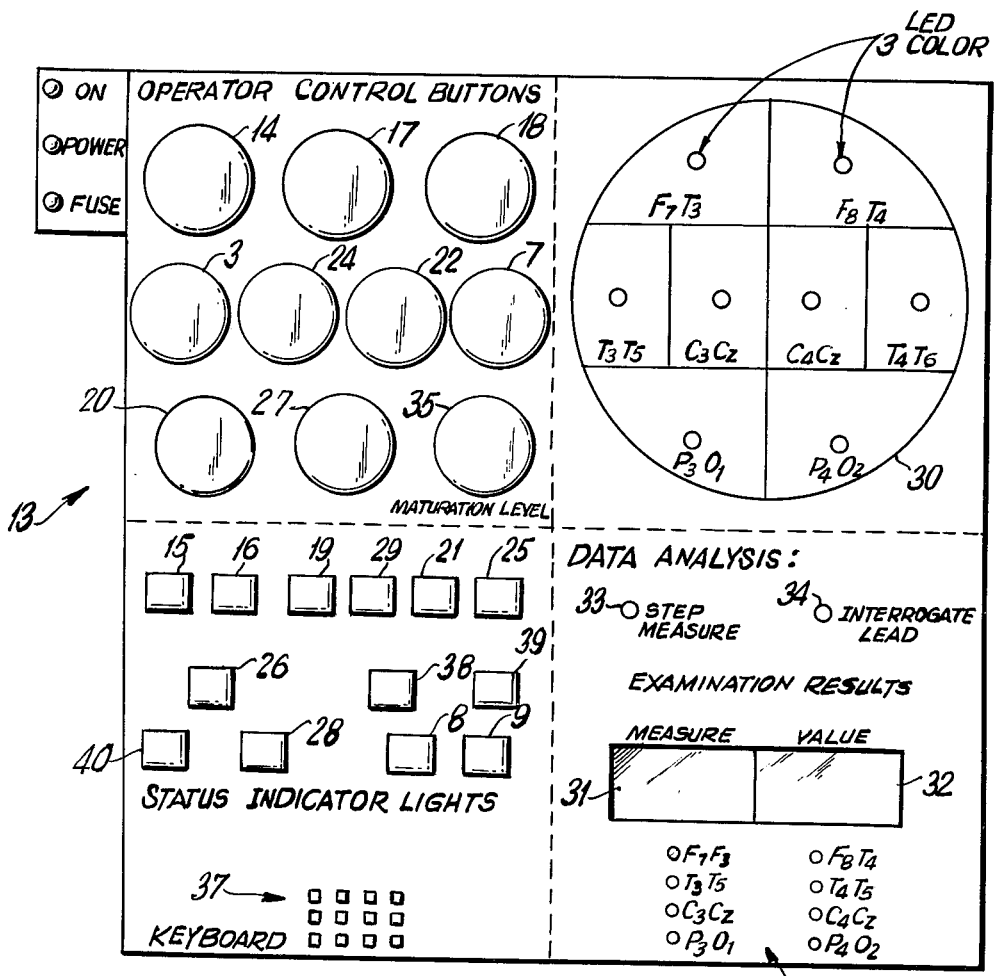
FIG. 2 is a top view of the operator's control panel utilized in the present invention.

As illustrated in FIG. 2 the LED's are in a pattern 30 corresponding to the electrodes' position on the head of the subject, as seen from above. If the impedance on all electrodes is acceptable, i.e., below a preset value, for example, 5000 ohms, then the light 16, indicating "impedance OK", lights up on the control panel 13. The impedance is initially tested by the operator. However, in addition, the same impedance test is carried out under control of the central processing unit (CPU) automatically whenever there is an interruption due to artifact, the impedance test occurring during the one-second interval after the artifact interruption. At any time that such a test is unacceptable for any lead data acquisition is interrupted and the occurrence of unacceptable impedance is indicated as described above. In addition, the impedance test is automatically repeated at the end of the testing period to insure that the data are completely acceptable.

One of the largest problems in the testing of subjects to obtain satisfactory EEG data arises because of voluntary and involuntary movement, especially by movements of the eyes (EOG) or of head and neck muscles (EMG). The computer system, if it is not able to discriminate and reject such movement, EOG and EMG artifacts, will react to the artifact as if it were a brain wave signal. Movement artifact is characterized by a large rapid signal and may be detected by a set of predetermined maximum threshold values which, if exceeded, indicate the presence of the artifact. Preferably the artifact reject will cancel out the signal during the time it is receiving signals in excess of the predetermined threshold. Another way to detect artifact makes use of the fact that the distribution of EEG amplitude is gaussian, and artifacts cause amplitudes which deviate significantly from such distributions. However, so-called "sharp waves" may also exceed these thresholds and should not be rejected as movement artifact.

The system of the present invention attempts to reduce the adverse effects of movement, EOG and EMG artifacts by treating each subject on an individual and dynamic basis. For each subject, a quiet period is obtained when the subject displays minimum or no movements, and a threshold level is set for the subject based upon that quiet period. More specifically, when the subject is motionless and relaxed, the operator pushes "set artifact level" button 17 on the panel 13. The object is to obtain 5 seconds of the subject's motionless and relaxed data when the subject's eyes are closed. The "set artifact level" button 17 is depressed for the 5-second period by the operator. However, if the subject moves or blinks during the 5 seconds, the operator releases the button and presses the memory reset button 18 to erase the data memory prior to gathering a new set of data.

The micro-computer (see FIG. 1) operates on the 5 seconds of data obtained from the relaxed and motionless subject, which is the data assumed to be the artifact-free data for that subject. An automatic calculation is made for each of the channels, including the EOG channel. When the computation is completed, the operator is informed that the artifact threshold has been set when "artifact threshold set" light 19 on panel 13 is illuminated. The computation for the artifact threshold is as follows: For each channel, the mean absolute amplitude (M) and standard deviation ($\sigma$) are computed.

Note that the normal EEG is gaussian with a mean value of zero volts. The artifact threshold is defined as $(+M+4\sigma)$ and $(-M-4\sigma)$ for each channel.

After the artifact level has been computed, the subject will then be tested to insure that the movement, EOG or EMG artifacts will in fact trigger the system. The operator depresses the "test artifact threshold" button 20 on the console panel 13. The subject is then requested to blink or contract his eyelids, move his eyes horizontally, move his eyes vertically, move his head, move his mouth and tongue, and move or clench his jaw. Each of these actions should be sufficient to trigger the "artifact detected" light 29. If the "artifact detected" light 29 is not lit after each of the actions, then the artifact level setting should be recomputed as it is likely to be too low. At the end of the six tests the "artifact threshold test okay" light 21 is illuminated, which indicates that the movement artifact tests have been successfully completed. If such tests are not successfully completed after three attempts, a set of preset threshold values is automatically imposed on the 8 channels and recording is carried out with those arbitrary thresholds.

In addition to the movement artifact, there is another phenomenon called a "sharp wave" which may cause the EEG data to deviate from gaussianity, but which is diagnostically important. In addition to mean amplitude, the mean first ($dV/dT$) and second ($d^2V/dT^2$) derivates of the EEG signal are computed for each sample and a sharp wave threshold level (button 24) is set for that subject in order to detect sharp waves which are above that threshold level. In general, sharp waves are electrical excursions 20 to 80 MS in duration which exceed predetermined limits of rise, for example (2 $\mu V/mS$), amplitude (50 $\mu V$), fall (2 $\mu V/MS$) and sharpness [$d^2V/dT^2$) $\mu 0°$] and which may occur in each electrode channel. These are possible epileptiform spikes. Sharp waves are defined in mathematical terms as $A > M_A + 3\sigma_A$ for 20 MS < "sharp wave" < 80 MS, $dV/dt > Mv'/dt + 3\sigma_{v'}$ or 2 $\mu v/MS$, $d^2V/dt^2 > M_{v''} + 3\sigma_{v''}$ or $<10°$. No true sharp wave can occur within 200 MS of any other sharp wave, and this condition is included in the definition. In these formulas $dV/dt = v'$, $d^2V/dt^2 = v''$.

To determine an individual subject's artifact and sharp wave thresholds, a segment 5 seconds long is gathered by the operator. This segment is sampled at 100/second and should apparently be artifact free, i.e., no movement was observed by the operator. Alternatively, the artifact threshold can be set first and used to exclude such artifact while the sharp wave threshold is determined. In either case, only the thresholds for the first 5 seconds are set this way; thereafter, the computer updates these thresholds every 5 seconds. The computer calculates the mean values of amplitude, dv/dt and $d^2_v/dt^2$, computed across the 5-second epoch (500 samples) for each channel, and also computes $\sigma A$, $\sigma_{v'}$, $\sigma_{v''}$ for the 5-second sample. Light 25, indicating "sharp wave threshold set", will light up on the control panel.

The operator is now ready to start the acquisition of data and does so by pushing the "start data acquisition" button 22. The data is acquired in 5-second segments of eyes closed EEG; each segment is placed in the buffer memory as 500 samples for each channel.

In the event that the initial movement artifact thresholds are not exceeded during the first 5-second sample, the corresponding 500 bytes of artifact-free data per channel are accepted for further processing, the movement artifact and sharp wave thresholds redefined for the next 5-second sample, and the 8 buffer registers are erased or replaced by 8 different buffer registers of 500 bytes each.

In the event that the initial movement artifact thresholds are exceeded during the first 5-second sample, the sample might be distorted by movement or muscle artifact or it may contain a sharp wave. In order to decide which is the case, the segment is evaluated by the sharp wave detector. There are 3 possibilities: (1) no sharp wave is detected in the segment. In this case, the segment is rejected as contaminated by movement artifact; (2) a sharp event is detected which exceeds the defined sharp wave threshold but is followed by another such sharp event in less than 200 mS. In this case, the segment is rejected as contaminated by muscle artifact because the EMG can produce sharp waves in the 20-50 Hz frequency range; (3) a sharp event is detected which exceeds the defined sharp wave threshold but is not followed by another sharp event before 200 mS elapses. In this case, the segment is accepted as artifact-free EEG containing a suspicious sharp wave. The presence of the suspect sharp wave is recorded in the sharp wave register corresponding to the channel or channels in which sharp waves were detected. In all three cases, the 8 buffer registers are then erased or replaced after updating the movement and sharp wave threshold definitions for the next 5-second segment. This procedure is iterated until a satisfactory body of data has been accumulated.

The 8 buffers are connected to the memory portion of the computer, with the memory portion being divided into 8 EEG data sections. Each of the sections contains 6,000 bytes, which provides for 60 seconds of artifact-free data at 100 points per second. In other words, if a subject is artifact free for a one-minute period, then the data section will be completely filled. It may happen, however that artifacts will occur, in which case the data section will take more than one minute to fill up. The data acquisition continues until the data sections are completely filled with valid data. At that time the light designating the "data acquisition completed" signal, which is light 26, goes on at the panel 13. Lights 38 and 39 go on in accordance with data acceptability and unacceptability, respectively.

The memory system described above, using a 60-second EEG sample which may be divided in twelve 5-second segments, is based upon storing the complete results of an analysis in the computer memory and then performing the computations later, after the subject is disconnected from the device. It may require, for example, a 48 K memory size, not including program memory. The total memory would be, for example, 64 K. This version minimizes the time required for testing. A less costly alternative, because it uses less memory capacity, would be to gather data for a short period, for example, 5 seconds, extract the data and perform the required computations on each 5-second segment of data and then store the computed results, for example, 72 numbers representing the relative power in each channel in each frequency band, and the coherence and asymmetry within each band for homologous leads. That procedure would be repeated a number of times, for example, 12 times. However, that alternative would require a longer testing period, since the subject would be kept waiting during the computations. One may use this alternative with a computer system having a smaller memory capacity, for example, 16 K, with only 4 K used for the data acquisition (500 bytes in each of 8 sections). This less costly alternative is adapted to locations having relatively low case loads, for example, a pediatrician's office.

The analysis of the data is in accordance with a predetermined set of power bands. Each of the channels is analyzed as 6 bands over the range 0.5 Hz to 50 Hz. The relative power in each of these bands has been documented by extensive studies to vary systematically during normal development. They are not arbitrarily chosen but have been selected based upon research to be maximally sensitive to the physiological states of subjects. The data from each channel is consequently analyzed to yield:

--- a 1. Absolute power in 0.5-1.5 Hz band ($\Delta 1$) - lower portion of delta
a 2. Absolute power in 1.5-3.5 Hz band ($\Delta 2$) - upper portion of delta
a 3. Absolute power in 3.5-7.5 Hz band ($\theta$) -theta
a 4. Absolute power in 7.5-12.5 Hz band ($\alpha$) - alpha
a 5. Absolute power in 12.5-25 Hz band ($\beta 1$) - lower portion of beta
a 6. Absolute power in 25-50 Hz band ($\beta 2$) - upper portion of beta
a 7. Pearson product moment or the polarity coincidence correlation coefficient between channels 1 & 2, 3 & 4, 5 & 6, 7 & 8 in order to provide an indication of waveshape asymmetry. Alternatively, the coherence of power in each of the 6 frequency bands may be computed between those pairs of symmetrical channels.
a 8. Total power in each channel in $\mu$ volts squared.
a 9. Total power ratio between channels 1 & 2, 3 & 4, 5 & 6, 7 & 8 in order to provide an indication of power asymmetry.
a 10. Band power ratio in each frequency band ($\Delta_2$, $\theta$, $\alpha$, $\beta_1$)
a 11. The total number of sharp waves detected in each channel.

---

If the absolute power in any channel for $\Delta_1 > \Delta_2$ or for $\beta_2 > \beta_1$, or if $\Delta_1$ or $\beta_2$ exceeds some absolute threshold to be entered after experimental definition, a light 40 on the panel should go on indicating "data may be contaminated by artifacts." Most movement artifacts lie in the 0.1-1.1 Hz range (within band $\Delta_1$) and EMG's lie in the 25-50 Hz range (within band $\beta_2$). If possible, the entire test sequence should be repeated. However, if the patient is too uncooperative, notation should be made on hard copy to effect that data may not be valid.

If the data appears to be valid, i.e., free of artifact then analysis should proceed as follows:

1. Total power in 1.5-25 Hz band should be computed.
2. Relative power (%) in $\Delta_2$, $\theta$, $\alpha$, $\beta_1$ should be computed (relative to total power defined as in 1)
3. If power in each band is Xi, $$\log \frac{(Xi)}{(100 - Xi)}$$

should be computed for each band in each channel.

4. For measures a.7, a.8, a.9 and a.10, log Xi should be computed.

Preferably at the beginning of the examination, the age of subject to 2 decimal places *minus one* should be entered as value of t. The operator enters age by pushing button 27 (labeled t), entering the age on keyboard 37 (0-9) and decimal point. At the beginning of the exam the keyboard 37 is also used to enter the subject number, the operator's number and the examination date.

Normative Polynomial Functions For EEG Variables

The table below (Table I) provides coefficients of 16 4th order polynomials $\overline{Y_i} = a_0 + a_1 t + a_2 t^2 + a_3 t^3 + a_4 t^4$ for each frequency band. These 16 polynomials predict the relative power in each frequency band for every one of the 8 derivations recorded, as a function of age. The value of standard deviation corresponding to each measure is a different constant for each derivation, also given in the table. A calibration constant c is defined, which must be empirically determined for any system performing these operations.

Z-Transforms

Z transformation is defined by the differences between the subject's values and mean values for the control group, divided by the standard deviation (S.D.) of the control group. This transform characterizes the deviation of the subject value from the control means as a multiple of the S.D., formulated as the following:

$$Z = \frac{x_i - \overline{X}}{\sigma x}$$

where Z represents a neurometric measure equal to the difference between the subject's individual score $X_i$ and the control group mean value, $\overline{X}$, divided by the S.D. of the whole sample; $\sigma_x$ refers to the deviation of scores of individuals in the control about the control group mean computed according to:

$$\sigma x = \sqrt{(X - \overline{X})^2}$$

where X is the value of the individual controls and $\overline{X}$ is the average value of the control group.

Z-transforms constitute a common metric of relative probability as the units in which all scores are stated, no matter what their initial dimensionality (i.e., frequency, amplitude, synchronization, symmetry).

The Z-transform for each measure a.1 to a.10 is computed:

$$Z = \frac{Y_i - \overline{Y_i} - C_i}{\sigma i}.$$

For measures a.1 to a.6, the polynomials in Table I or a corresponding set of normative data can be used. For a.7 to a.10 a normative data set is stored in the memory of the device.

In the present instance, $Y_i$ is the value of each measure computed from the subject, $\overline{Y_i}$ is the value of the corresponding measure competed from the polynomial, $C_i$ is the calibration constant computed according to the appropriate calibration procedure, and $\sigma i$ is the value of the corresponding standard deviation.

The Z-values are preferably coded as follows:
$Z < +1.96$ for $\Delta_2, \theta, \beta_1$ = level 0 (green L.E.D.);
$Z \geq +1.96$ for $\Delta_2 \theta, \beta_1$ = level 1.0 (amber L.E.D.);
$Z \geq +2.5$ for $\Delta_2, \theta, \beta_1$ = level 2.0 (red L.E.D.);
$> -1.96$ for $\alpha$ = level 0 (green L.E.D.);
$Z \leq -1.96$ for $\alpha$ = level 1.0 (amber L.E.D.);
$Z \leq -2.50$ for $\alpha$ = level 2.0 (red L.E.D.);
Note: $Z \geq |1.96|$ indicates the 0.05 significance level. $Z \geq |2.5|$ indicates the 0.01 significance level. A light 28 on the panel goes on to indicate "analysis completed."

MATURATIONAL LAG AND DEVELOPMENTAL DEVIATION

The 16 polynomial functions describe the evolution with age of the distribution of the relative power of the EEG into the 4 frequency bands for 4 anatomical regions on each side of the head. After Z-transformation of the subject's data, the resulting 4 Z-values for each region can be used to define the vector distance $\overline{Z}$ between the actual data and the predicted mean values for a normal healthy person of the same age:

$$\overline{Z} = (Z_{delta}^2 + Z_{theta}^2 + Z^2\text{alpha} + Z^2\text{beta})^{\frac{1}{2}}$$

It is now possible to ask whether the value of $\overline{Z}$ can be made acceptably small (e.g. $\leq 1.96$) by comparing the actual data to the values predicted by the polynomials at any age. This is the same as asking whether there is any age at which the distribution of relative power, actually observed in any region, would be considered within normal limits based on the known distribution of Z in a population of healthy children of that age. If there is an abe for which the observed value of Z would have been within normal limits, then that age is considered to be the maturation level of the brain region from which the actual data were recorded. If this maturation level is different from the age of the subject, the discrepancy in years is termed the *maturational lag*. If the value of Z cannot be brought within acceptable limits no matter what value of t is introduced in the polynomial function, that brain region is considered to display a *developmental deviation*. Provision is made on the console to display these results (button 35) region by region. The "maturation level" button is depressed followed by depression of the button/light 36 for the appropriate brain region, and the maturational lag, if any, appears in the display 32. If the region displays a developmental deviation, the symbol "DD" appears in display 32.

FIG. 2 shows a preferred type of console for use in the present invention. The console contains a head diagram 30 with one sector corresponding to each of the eight channels. The sectors are labeled with the electrode leads corresponding to each of the channels. A 3-color lamp means L.E.D. (red-amber-green) illuminates each sector of the head diagram. The console panel contains a digital L.E.D. display 31 labeled "measure", which enumerates the measures a.1 to a.11. A digital L.E.D. readout 32, labeled "value", provides the value of the Z-transform for each lead 1-8 for the indicated analysis.

Once the analysis is complete, depression of the "step" button 33 steps the "Examination Results" display 31 through the sequence of measures a.1 to a.11. Depression of the "Interrogate Lead" button 34 steps through the values of the Z-transform for each lead for the analysis indicated in 31, while the lights 36 indicate which lead is being interrogated. If the computed value for a given head region, corresponding to a sector in head diagram 30, is within normal limits, the L.E.D. for that sector is green. If the value is between $p = 0.05$ and $p = 0.01$, the L.E.D. is amber and, if the value is less than $p = 0.01$ then the L.E.D. is red.

Alternatively, once analysis is over, the test operator can enter measure a1 on the alpha-numeric keyboard 37, observe the display on the L.E.D. head diagram 30, and enter the results on a hard copy (paper) diagram. If precise Z-values are desired, they are provided by the digital readout 32, interrogated by button 34. He then presses "data reset" button 3 and enters measure a2 on the keyboard. He observes the display and records the result for measure 2. He then proceeds in the same manner with the other measures $a^3$–$a^8$ until the record is complete.

The procedure and equations of the present invention constitute a method to utilize knowledge of the quantitative rules governing the maturation in the normal brain of the EEG parameters specified herein for practical diagnostic purposes in routine clinical applications. Experimental findings indicate that the values obtained in measures of these parameters are a replicable feature of the individual. Those results further indicate that these rules are generally applicable, independent of cultural, ethnic, socioeconomic, age or sex factors. The results also indicate that these EEG parameters are stable; that they reveal few false positives beyond the chance level in healty children; and that they are extremely sensitive to neurological diseases and brain dysfunctions related to learning disabilities.

Modifications may be made in the present invention within the scope of the subjoined claims. For example, the normative relative power data which is derived from the normal population, instead of being in the form of a formula, may be in the form of stored normative tables. Such tables are stored in the memory portion of the microprocessor 12. Preferably the normative tables do not provide data which is age-related to each month, but rather provide such data which is only age-related to the age in years. A simple interpolation algorithm may then be used to derive the normative data from the tables based upon the age in months as well as years of the subject under test.

fuse or localized shifts in the EEG spectrum, the method comprising:

removably securing a plurality of electrodes to the head of said subject under test, providing multiple channels of information with each channel being from a different head region;

amplifying the on-going signals representing brain waves from each of said head regions while the subject sits relaxed with a minimum of external stimuli;

converting the said amplified signals into digital form;

dividing the digital form brain wave signals into a plurality of frequency bands; computing the power in each of said frequency bands for each head region to provide frequency band relative (%) power; automatically comparing said relative power in each frequency band with a set of normative relative power data derived from a normal population using the formula:

$$a_0 + a_1 t + a_2 t^2 + a_3 t^3 + a_4 t^4$$

where t is age related and the coefficients $A_o \ldots a_4$ are determined by data from the normal population, where a different polynomial is used to define the relative power expected in each frequency band in each head region;

computing the Z-transform of each subject value relative to the means and standard deviations of the normative data; and displaying the results for each subject of such computation for each of said different head regions at each of said frequency bands.

2. The method of electroencephalography of claim 1

TABLE I

Coefficients of Fourth Order Polynomial Regression Functions for Logarithmic Transform of Relative Power

| | C0 | C1 | C2 | C3 | C4 |
|---|---|---|---|---|---|
| F7-T3 and F8-T4 | | | | | |
| Delta | 0.05026793 | −0.02864339 | 0.00268197 | −0.00024649 | 0.00000726 |
| Theta | −0.49661124 | 0.02704753 | −0.00219526 | −0.00012897 | 0.00000637 |
| Alpha | −1.19101954 | 0.11536730 | −0.01021430 | 0.00052462 | −0.00001035 |
| Beta | −0.69595569 | −0.05826711 | 0.00636409 | −0.00002820 | −0.00000592 |
| Cz-C3 and Cz-C4 | | | | | |
| Delta | 0.01337487 | −0.11086171 | 0.01164788 | −0.00062616 | 0.00001153 |
| Theta | −0.39715552 | 0.07269696 | −0.01230534 | 0.00065100 | −0.00001268 |
| Alpha | −0.94571376 | 0.17154604 | −0.01993426 | 0.00110665 | −0.00002212 |
| Beta | −0.95783710 | −0.09368554 | 0.01825462 | −0.00099472 | 0.00001902 |
| T3-T5 and T4-T6 | | | | | |
| Delta | 0.01312087 | −0.10731703 | 0.01305750 | −0.00081664 | 0.00001665 |
| Theta | −0.41266653 | 0.10212188 | −0.02114789 | 0.00119691 | −0.00002312 |
| Alpha | −1.22848630 | 0.18772255 | −0.01056178 | 0.00017109 | 0.00000299 |
| Beta | −0.70206171 | −0.10165458 | 0.01017377 | −0.00014639 | −0.00000520 |
| P3-O1 and P4-O2 | | | | | |
| Delta | 0.14496185 | −0.20564358 | 0.02497562 | −0.00150341 | 0.00003163 |
| Theta | −0.41780865 | 0.13641311 | −0.03206439 | 0.00204809 | −0.00004317 |
| Alpha | −1.14453661 | 0.25399819 | −0.02050309 | 0.00080608 | −0.00001157 |
| Beta | −1.06820560 | −0.06939101 | 0.01273942 | −0.00057574 | 0.00000711 |

Standard Deviations of Log Relative Power for each Frequency Band in Every Derivation

| | Central | Temporal | Parieto-occipital | Fronto-temporal |
|---|---|---|---|---|
| Delta | 0.17550 | 0.19515 | 0.22553 | 0.13585 |
| Theta | 0.19706 | 0.21789 | 0.21229 | 0.13763 |
| Alpha | 0.27472 | 0.25411 | 0.26090 | 0.18157 |
| Beta | 0.14968 | 0.20643 | 0.17554 | 0.19110 |

What is claimed is:

1. A method in electroencephalography for testing subjects to determine organic brain dysfunction by diffuse or localized shifts in the EEG spectrum, the method comprising:

wherein said electrodes comprise pairs of electrodes from portions of the subject's head and said display is in sectors corresponding to the said head portions.

3. The method of electroencephalography of claim 1 wherein said plurality of frequency bands are four bands.

4. A method in electroencephalography for testing subjects to determine organic brain dysfunction by diffuse or local shifts in the EEG spectrum, the method comprising:
- removably securing a plurality of electrodes to the head of said subject under test, providing multiple channels of information with each channel being from a different head region;
- amplifying the on-going signals representing brain waves from each of said head regions while the subject sits relaxed with a minimum of external stimuli;
- converting the said amplifier signals into digital form;
- dividing the digital form brain wave signals into a plurality of frequency bands; computing the power in each of said frequency bands to provide frequency band relative (%) power; automatically comparing said relative power in each frequency band with a set of normative relative power data derived from a normal population and related in age to the subject;
- computing the Z-transform of each subject value relative to the means and standard deviations of the normative data; and
- displaying the results for each subject of such computation for each of said frequency bands according to the head locations tested.

5. The method of electroencephalography of claim 4 wherein said set of normative relative power data is a normative table contained in computer memory.

6. A method in electroencephalography as in claims 1, 2, 3, 4 or 5 in which the vector sum $\bar{Z}$ of the univariate deviations $Z_\Delta$, $Z_\theta$, $Z_\alpha$ and $Z_\beta$ ($Z=|Z_\Delta^2+Z_\theta^2+Z_\alpha^2+Z_\beta^2|^{\frac{1}{2}}$) is computed for the relative power in the $\Delta$, $\theta$, $\alpha$ and $\beta$ frequency bands in each region; in which the normative equations or tables are scanned to ascertain the electrophysiological age $t_{EEG}$ at which $\bar{Z}$ falls within an acceptable range determined from the population of normal values; in which the discrepancy between the actual age of the subject $t_{ACTUAL}$ and the apparent electrophysiological age $t_{EEG}$, $t_{ACTUAL}-t_{EEG}$ is calculated to define the maturational lag for each brain region; and in which the region is defined as displaying a developmental deviation if the value of $\bar{Z}$ is not acceptably small for any value of t.

7. A system in electroencephalography for screening of subjects to determine organic brain dysfunction by diffuse or local shifts in the EEG spectrum, comprising:
- a plurality of electrodes removably secured to the head of said subject to detect the brain waves of the subject and connected to selected different regions of the subject's head;
- means for simultaneously amplifying the brain wave signals from each of said electrodes;
- means for converting the amplified signals into digital form;
- means for dividing the digital form brain wave signals from each of said selected head regions into a plurality of frequency bands, computing the power in each of said bands at each of said head portions to provide regional frequency band relative (%) power; automatically comparing said regional frequency-band relative power with a set of normative results from a normal population using the formula:

$$a_0+a_1t+a_2t^2+a_3t^3+a_4t^4$$

where t is age related and the coefficients $a_0 \ldots a_4$ are determined by the data from the normal population;
- means for computing the Z-transform of each subject value relative to the means and standard deviations of the normative results; and
- means to display the results of the said Z-transform computation.

8. A system in electroencephalography as in claim 7 wherein said display means includes portions of illuminable panels corresponding in location to the said local selected head areas, and means to light each panel portion with a light whose color depends upon the results of the said computation.

9. A system in electroencephalography for screeing of subjects to determine organic brain dysfunction by diffuse or local shifts in the EEG spectrum, comprising:
- a plurality of electrodes removably secured to the head of said subject to detect the brain waves of the subject and connected to selected different regions of the subject's head;
- means for simultaneously amplifying the brain wave signals from each of said electrodes;
- means for converting the amplified signals into digital form;
- means for dividing the digital form brain wave signals from each of said selected head regions into a plurality of frequency bands, computing the power in each of said bands at each of said head portions to provide regional frequency band relative (%) power; computer memory means for storing age-related normative tables of relative (%) power for each of said frequency bands; means for automatically comparing said regional frequency-band relative power with normative results from a normal population using said stored normative tables;
- means for computing the Z-transform of each subject value relative to the means and standard deviations of the normative results; and
- means to display the results of the said Z-transform computation.

10. A system in electroencephalography as in claim 9 wherein said display means includes portions of illuminable panels corresponding in location to the said local selected head areas, and means to light each panel portion with a light whose color depends upon the results of the said computation.

11. A system in electroencephalography as in claims 7, 8, 9 or 10 in which the vector sum Z of the univariate deviations $Z_\Delta$, $Z_\theta$, $Z_\alpha$ and $Z_\beta$ ($Z=|Z_\Delta^2+Z_\theta^2+Z_\alpha^2+Z_\beta^2|^{\frac{1}{2}}$) is computed for the relative power in the $\Delta$, $\theta$, $\alpha$ and $\beta$ frequency bands in each region; in which the normative equations or tables are scanned to ascertain the eletrophysiological age $t_{EEG}$ at which Z falls within an acceptable range determined from the population of normal values; in which the discrepancy between the actual age of the subject $t_{ACTUAL}$ and the apparent electrophysiological age $t_{EEG}$, $t_{ACTUAL}-t_{EEG}$ is calculated to define the maturational lag for each brain region; and in which the region is defined as displaying a developmental deviation if the value of $\bar{Z}$ is not acceptably small for any value of t.

* * * * *